(12) United States Patent
Dicks et al.

(10) Patent No.: US 7,662,107 B2
(45) Date of Patent: Feb. 16, 2010

(54) USE OF 1,1,1,2-TETRAFLUOROETHANE FOR MEASURING LUNG FUNCTION, ESPECIALLY FOR DETERMINING THE FUNCTIONAL RESIDUAL CAPACITY (FRC) OF THE LUNGS

(75) Inventors: Bernd Michael Dicks, Lübeck (DE); Jochim Koch, Ratzeburg (DE)

(73) Assignee: Dräger Medical AG & Co. KG, Lübeck (DE)

( * ) Notice: Subject to any disclaimer, the term of this patent is extended or adjusted under 35 U.S.C. 154(b) by 297 days.

(21) Appl. No.: 11/464,264

(22) Filed: Aug. 14, 2006

(65) Prior Publication Data
US 2007/0053841 A1    Mar. 8, 2007

(30) Foreign Application Priority Data
Sep. 3, 2005    (DE) ......................... 10 2005 041 905

(51) Int. Cl.
*A61B 5/08*    (2006.01)
(52) U.S. Cl. .................. 600/532; 600/529; 600/538
(58) Field of Classification Search .............. 600/531, 600/532
See application file for complete search history.

(56) References Cited

U.S. PATENT DOCUMENTS 4,955,371 A * 9/1990 Zamba et al. .......... 128/200.18
6,254,546 B1 * 7/2001 Vierto-Oja ................ 600/529
6,544,191 B2 * 4/2003 Koch et al. ................ 600/538

FOREIGN PATENT DOCUMENTS

DE        10046465 A1    4/2002

OTHER PUBLICATIONS

Emmen et al. "Human safety and pharmacokinetics of the CFC alternative propellants HFC 134a (1,1,1,2-tetrafluoroethane) and HFC 227 (1,1,1,2,3,3,3-heptafluoropropane) following whole-body exposure". Regul Toxicol Pharmacol. Aug. 2000; 32(1):22-35. Abstract only.*
Victor W. Pikes et al.; Disposition of Inhaled 1, 1, 1, 2-Tetrafluoroethane (HFA134A) in Healthy Subjects and in Ptients With Chronic Airflow Limitation; Measurement by 18F-Labeling and Whole-Body gamma-counting; Drug Metabolism and Disposition, Bd. 23, Nr. 8, 1995, Seiten 832-839, XP008104470; pp. 832-839.

* cited by examiner

*Primary Examiner*—Patricia C Mallari
(74) *Attorney, Agent, or Firm*—McGlew and Tuttle, P.C.

(57) ABSTRACT

1,1,1,2-Tetrafluoroethane (norflurane) is used as a tracer/trace gas for measuring the lung function because of its simple detectability, physiological harmlessness, environmental friendliness and ready availability. Especially advantageous is the possibility of the optical concentration measurement of 1,1,1,2-tetrafluoroethane for the measurement of the lung function and especially for the determination of the FRC during respiration during anesthesia, without cross sensitivity occurring during the measurement with respect to anesthetics.

15 Claims, 1 Drawing Sheet

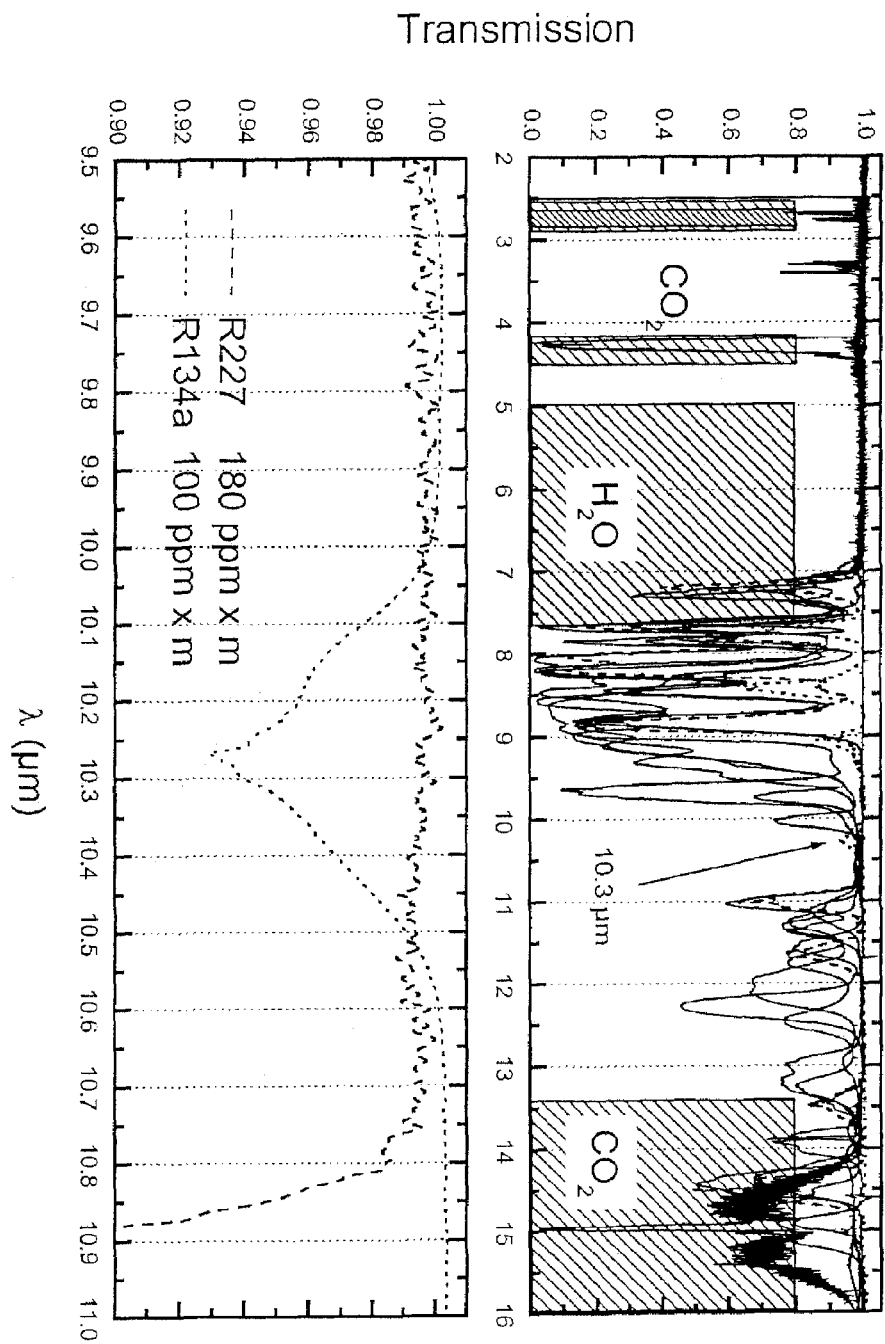

ial effort due to the mass spectrometric determination to be used, and others, for example, sulfur hexafluoride, have no medical approval for medical use in most countries.

USE OF 1,1,1,2-TETRAFLUOROETHANE FOR MEASURING LUNG FUNCTION, ESPECIALLY FOR DETERMINING THE FUNCTIONAL RESIDUAL CAPACITY (FRC) OF THE LUNGS

CROSS REFERENCE TO RELATED APPLICATIONS

This application claims the benefit of priority under 35 U.S.C. § 119 of German Patent Application DE 10 2005 041 905.4 filed Sep. 3, 2005, the entire contents of which are incorporated herein by reference.

FIELD OF THE INVENTION

The present invention pertains to the use of 1,1,1,2-tetrafluoroethane for measuring the lung function, especially for determining the functional residual capacity (FRC) of the lungs during respiration.

BACKGROUND OF THE INVENTION

The measurement of the lung function and especially the determination of the FRC during respiration (also known as ventilation) with the use of fluoropropane, namely, heptafluoropropane, hexafluoropropane or perfluoropropane as trace/tracer gases appears from DE 100 46 465 B4 and the equivalent U.S. Pat. No. 6,544,191 B2, so that reference is explicitly made to these prior publications for the method of lung function measurement and FRC determination (DE 100 46 465 B4 and U.S. Pat. No. 6,544,191 B2 are hereby incorporated by reference in their entirety).

A method for determining properties of the lungs outside of mechanical respiration by means of the bolus dosage of a mixture of different gases soluble in the blood, in which the measurement is evaluated by means of an optimization algorithm, for the expiratory gas concentrations measured subsequent to the inhalation, is described in U.S. Pat. No. 6,254,546 B1.

Moreover, various other trace gases have been used for the measurement of the FRC, these gases being added to the breathing gas, in general, in amounts of a few volume percentages (vol. %), as a result of which the harmful effect on the health of the patient being respirated and examined is very extensively reduced. The drawback of the trace/tracer gases used hitherto is the high purchase price and the generally great technical effort with which the trace gases used are filled and applied, with the consequence that diagnostic procedures for determining the lung function by means of trace gases have become established so far in niche markets only, such as high-performance sports medicine, and, in particular, they do not belong to the clinical routine in the case of mechanically respirated patients in intensive care units. Some trace gases, for example, helium, require, moreover, a great measuring technical effort due to the mass spectrometric determination to be used, and others, for example, sulfur hexafluoride, have no medical approval for medical use in most countries.

SUMMARY OF THE INVENTION

Thus, the object of the present invention is to select a trace gas for use for lung function measurement and especially for determining the FRC of the lungs of a patient or volunteer during respiration, which can be detected in a simple manner, is physiologically harmless, environmentally friendly and is available at a low cost.

According to the invention, the fluorohydrocarbon 1,1,1,2-tetrafluoroethane with the formula $F_3C$—$CH_2F$ and the corresponding empirical formula $C_2H_2F_4$, INN name norflurane is used as a trace gas in a method for measuring lung function. 1,1,1,2-tetrafluoroethane is widely used in practice worldwide and is approved for medical purposes, but has not yet been used for FRC measurement. Another name for 1,1,1,2-tetrafluoroethane is "R 134a."

Essential advantages of 1,1,1,2-tetrafluoroethane, also compared to 1,1,1,2,3,3,3-heptafluoropropane (another name: "R 227"), which is also approved for medical purposes, are:

An optical absorption line at 10.3 μm, where the cross sensitivity to anesthetics occurring during mechanical respiration during anesthesia and to laughing gas ($N_2O$) is extensively reduced; and A low purchase price of "R 134a" compared to "R 227" because of the simpler manufacturing process and the more widespread use as well as the better environmental friendliness with a lower "Global Warming Potential" (GWP) relative to $CO_2$, equaling 1,300 ("R 227"=2,900).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a graph of the absorption spectra of the different known anesthetic gases (enflurane, isoflurane, sevoflurane, desflurane, halothane) and laughing gas ($N_2O$) plotted over the wavelength in the upper part, and the absorption spectra of the fluorohydrocarbons 1,1,1,2-tetrafluoroethane ("R 134a") as well as 1,1,1,2,3,3,3-heptafluoropropane ("R 227") are shown in the lower part.

DESCRIPTION OF THE PREFERRED EMBODIMENTS

Referring to the drawings in particular, as it can be recognized from the only FIGURE 1,1,1,2-tetrafluoroethane has an optical absorption line at 10.3 μm. With this the cross sensitivity to anesthetics occurring during mechanical respiration during anesthesia and to laughing gas ($N_2O$) is extensively reduced. The only FIGURE also shows the absorption spectra of the different known anesthetic gases (enflurane, isoflurane, sevoflurane, desflurane, halothane) and laughing gas ($N_2O$) are plotted over the wavelength $\lambda$ in the upper part. The absorption spectra of the fluorohydrocarbons 1,1,1,2-tetrafluoroethane ("R 134a") as well as 1,1,1,2,3,3,3-heptafluoropropane ("R 227") are shown in the lower part. It is seen from the FIGURE that when "R 134a" is used, infrared concentration measurements are readily possible on the basis of the characteristic absorption peak at 10.3 μm even in the presence of volatile anesthetics and laughing gas ($N_2O$), whereas this is not possible for "R 227."

The tracer gas can be used either directly from an inhaler in the form of a bolus dosage during respiration or by means of an inserted dispensing unit, which is operated continuously or intermittently and optionally mixes the tracer gas with other breathing gases in the anesthesia apparatus or respirator. The inhalant is, for example, a drug, whose composition contains "R 134a" as an additive to a ready-made inhalation solution or a partial quantity of the composition, which likewise contains "R 134a."

As is known from the state of the art, the determination of the FRC is carried out with "R 134a" as a trace/tracer gas especially by a combination of volume and concentration measurement with a corresponding evaluation, as it is described in DE 100 46 465 B4 and U.S. Pat. No. 6,544,191 B2.

The determination of the FRC is carried out on mechanically respirated patients. By measuring other components of the inhalation composition, it is optionally possible to calculate other functional variables, which are known per se, such as the "pulmonary blood flow," and a compartmental analysis of the lung can also be carried out as follows:

If the end-expiratory concentrations are plotted semilogarithmically over the number of breaths since the beginning of washout after washout of the tracer gas, a multilineal curve is obtained, in general. Each linear component corresponds to a washout time constant and can be assigned to a lung compartment. Every individual compartment is characterized by a volume and an effective tidal volume, the sum of the volumes of all compartments yielding the FRC and the sum of the effective tidal volumes of all compartments yielding the effective tidal volume of the lungs for the washout being considered (parallel connection). The calculation of the tidal volumes makes sense above all during regular spontaneous breathing or mandatory mechanical respiration, because the tidal volumes remain nearly constant over the washout in these cases.

For example, the following time curve of the end-expiratory concentrations is obtained for a lung with two compartments, the subscript I designating the number of breaths since the beginning of washout, c(0) being the known initial concentration in the lung and $\lambda_1$ and $\lambda_2$ being the decay rates of the two compartments, which disintegration rates are to be determined:

$$c(i)=c(0)\cdot e^{-\lambda_1 i}+c(0)\cdot e^{-\lambda_2 i}$$

Decadic logarithms of the concentration and standardization to the initial concentration yields:

$$\log_{10}(c(i)/c(0))=\log_{10}(e^{-\lambda_1 I}+e^{-\lambda_2 i})=-\lambda_1\cdot i\cdot(\log_{10}e)+\log_{10}(1+e^{(\lambda_1-\lambda_2)i})$$

If we assume, without limitation of generality, that $\lambda_1 > \lambda_2$, i.e., that $\lambda_1$ represents the dominant disintegration rate (most rapid disintegration), the first linear component can be extracted (first summand on the right-hand side in the above equation). Since the term in the exponent of the second summand is positive and increases with increasing I, the 1 in the logarithm may be ignored for high values of I (toward the end of washout). For high values of I, we approximately obtain $$\log_{10}(c(i)/c(0))\approx-\lambda_1\cdot i\cdot(\log_{10}e)+(\lambda_1-\lambda_2)\cdot i\cdot(\log_{10}e)=-\lambda_2\cdot i\cdot(\log_{10}e)$$

The unknowns are thus determined for the two-compartment model. In case of more than two compartments, $\lambda_2$ must be replaced by the sum of all disintegration rates with the exception of $\lambda_1$. The analysis will then show the lowest disintegration for high values of I (end of washout); this disintegration rate can be eliminated by subtraction in the initial equation. The second lowest disintegration is subsequently determined in the semilogarithmic representation, etc. The greater the ratio of the highest to the lowest disintegration rate, the greater is the inhomogeneity of the lungs.

If the dead volume was subtracted beforehand, the following relationships are obtained for the disintegration rates and the volumes of the compartments:

$$\lambda_j = V_{Tj}/V_j$$

$$FRC = \sum_j V_j$$

$$V_T = \sum_j V_{Tj}$$

Here, $VT_j$ designates the effective tidal volume for the jth compartment, and $V_j$ the volume of the jth compartment. The following simple relationships are obtained from this for the two-compartment model:

$$V_{T1} = \frac{V_T - \lambda_2 \cdot FRC}{1 - \lambda_2/\lambda_1} \quad V_1 = V_{T1}/\lambda_1$$

$$V_{T2} = \frac{\lambda_1 \cdot FRC - V_T}{\lambda_1/\lambda_2 - 1} \quad V_2 = V_{T2}/\lambda_2$$

In addition, by determining the quantity of the washed-out tracer gas on the basis of the known inhalation composition, a possibility is obtained to calculate the quantity of medically active components that have entered the lungs, as a result of which more exact dispensing of inhalation drugs becomes possible than before.

Another possible use is in the alternating or simultaneous inhalation of "RR 134a" or "R 227" in order to use the differences in the solubilities of the two fluorohydrocarbons in the blood for the diagnostic testing of the lung function.

The solubility of gases in the blood can be described by the blood-gas partition coefficient L, which describes the ratio of the volume percentages between gas dissolved in the blood and gas present in the gas phase. The prerequisite for this is the presence of an equilibrium with identical partial pressures of the gas in the phase in which it is dissolved in the blood and in the gas phase. Lowest possible solubility of the tracer gas in the blood is desirable for the lung function diagnostic tests and especially for the determination of the FRC, because what we wish to ultimately determine is the lung volume rather than the quantity of blood in the body. By using at least two gases with different solubilities in blood, the FRC measurement can be corrected with respect to the solubility in blood. The subscripts 1 and 2 below designate the two gases, which may stand, e.g., for R 134a and R 227.

If we assume that not only the concentration in the lung is at equilibrium for the FRC measurement, but that the concentration in the blood has also reached its equilibrium value, an FRC determination leads to different values as a function of the solubility in blood:

$$FRC_j = FRC + V_{blood} \cdot L_j.$$

The $FRC_j$ measured with the gas j is overestimated by the product of the blood volume in the body times the blood-gas partition coefficient L compared to the true value (designated by FRC here), Knowing the blood volume, a correction of the FRC determination can already be carried out with a gas of known solubility. Knowledge of the blood volume is not necessary if a second gas is used.

It can be assumed below, without restricting the generality, that $L_1 > L_2$, so that the FRC measured with gas 1 (for example, R 134a) will be greater than that measured with gas 2 (for example, R 227). The blood volume can be determined from the difference of the FRC values:

$$V_{Blood} = \frac{FRC_1 - FRC_2}{L_1 - L_2}$$

This makes it possible to correct the FRC measurement, which is closer to the true value, with gas 2:

$$FRC = FRC_2 - \frac{FRC_1 - FRC_2}{L_1/L_2 - 1}$$

In case of R 134a and R 227, the coefficient $L_1/L_2$ is approx. 4, so that the measured difference in FRC is divided by 3.

In particular, the "pulmonary blood flow" can be estimated or the FRC determination can be corrected with respect to the quantity of tracer gas dissolved in the blood, besides the determination of the FRC.

The inhalation composition is especially a pressurized liquid composition with a drug dissolved therein for the therapy of asthma or for the therapy of other lung diseases and the dispensing being carried out by means of a spray dispenser, MDI (medical dose inhaler) during respiration. In particular, the application is carried out such that if the quantity taken up by the patient is assumed to be about 10% to 30% of the total quantity of gas metered per dispensing stroke, the concentration of 1,1,1,2-tetrafluoroethane alone or combined with 1,1,1,2,3,3,3-heptafluoropropane is about 1 vol. % to 5 vol. % and especially 0.1 vol. % to 1 vol. %, maximum, of the gas mixture present in the lungs after the inhalation.

While specific embodiments of the invention have been shown and described in detail to illustrate the application of the principles of the invention, it will be understood that the invention may be embodied otherwise without departing from such principles.

What is claimed is:

1. A method comprising:
   providing a gas including a breathing gas with 1,1,1,2-tetrafluoroethane as a trace gas;
   delivering said breathing gas with the 1,1,1,2-tetrafluoroethane trace gas to the lungs of a subject via one of an anesthesia apparatus and a respirator; and
   measuring lung function of the subject during inhalation with one of said anesthesia apparatus and said respirator based on the 1,1,1,2-tetrafluoroethane trace gas, wherein said step of measuring lung function includes determining the functional residual capacity (FRC) of the lungs.

2. A method according to claim 1, wherein FRC of the lungs is determined by washout.

3. A method according to claim 1, wherein the 1,1,1,2-tetrafluoroethane is a component of an inhalation composition used during respiration/anesthesia.

4. A method according to claim 3, wherein the inhalation composition includes at least one drug.

5. A method according to claim 1, wherein said gas includes said breathing gas with 1,1,2,3,3,3,-heptafluoropropane as another trace gas, wherein the quantity ratio of the two trace gases 1,1,1,2,3,3,3-heptafluoropropane:1,1,1,2-tetrafluoroethane ranges from 1:2 to 1:3 as the maximum.

6. A method according to claim 1, wherein concentration during respiration of the trace gas 1,1,1,2-tetrafluoroethane is about 1 vol. % to 5 vol. %, maximum of the inspired breathing gas volume present in the lungs.

7. A method according to claim 6, wherein concentration during respiration of the trace gas 1,1,1,2-tetrafluoroethane is 0.1 vol. % to 1 vol. % of the inspired breathing gas volume present in the lungs.

8. A method according to claim 1, wherein said gas includes said breathing gas with 1,1,2,3,3,3-heptafluoropropane as another trace gas, wherein concentration during respiration of the trace gas 1,1,1,2-tetrafluoroethane combined with 1,1,1,2,3,3,3-heptafluoropropane is about 0.1 vol. % to 1 vol. %, of the inspired breathing gas volume present in the lungs.

9. A method according to claim 1, wherein using the 1,1,1,2-tetrafluoroethane trace gas to measure lung function includes dispensing 1,1,1,2-tetrafluoroethane continuously per breath by means of a spray dispenser during respiration.

10. A method comprising:
    providing a gas including a breathing gas with 1,1,1,2-tetrafluoroethane as a trace gas and a predetermined concentration of 1,1,1,2,3,3,3-heptafluoropropane as another trace gas;
    delivering said breathing gas with the 1,1,1,2-tetrafluoroethane trace gas and the 1,1,1,2,3,3,3-heptafluoropropane trace gas to the lungs of a subject via one of an anesthesia apparatus and a respirator; and
    measuring lung function of the subject during inhalation with one of said anesthesia apparatus and said respirator based on the 1,1,1,2-tetrafluoroethane trace gas and the 1,1,1,2,3,3,3-heptafluoropropane trace gas, wherein a concentration during respiration of the trace gas 1,1,1,2-tetrafluoroethane combined with 1,1,1,2,3,3,3-heptafluoropropane trace gas is about 1 vol. % to 5 vol. %, maximum of the inspired breathing gas volume present in the lungs, said step of measuring lung function including determining a functional residual capacity (FRC) of the lungs of the subject.

11. A method comprising:
    providing a gas comprising a breathing gas with 1,1,1,2-tetrafluoroethane as a trace gas;
    delivering said breathing gas with the 1,1,1,2-tetrafluoroethane trace gas to the lungs of a subject via one of an anesthesia apparatus and a respirator; and
    measuring lung function of the subject during inhalation with one of said anesthesia apparatus and said respirator based on the 1,1,1,2-tetrafluoroethane trace gas, wherein the 1,1,1,2-tetrafluoroethane trace gas is dispensed continuously per breath by means of a spray dispenser during respiration, said step of measuring lung function including determining a functional residual capacity (FRC) of the lungs of the subject.

12. A method according to claim 1, wherein said breathing gas comprises 1,1,1,2,3,3,3,-heptafluoropropane as another trace gas, said breathing gas with said 1,1,1,2-tetrafluoroethane trace gas and said 1,1,1,2,3,3,3,-heptafluoropropane trace gas being delivered to the subject via one of said anesthesia apparatus and said respirator, said lung function being measured based on the 1,1,1,2-tetrafluoroethane trace gas and the 1,1,1,2,3,3,3-heptafluoropropane trace gas.

13. A method according to claim 12, wherein the quantity ratio of the two trace gases 1,1,1,2,3,3,3-heptafluoropropane:1,1,1,2-tetrafluoroethane ranges from 1:2 to 1:3 as the maximum.

14. A method according to claim 11, wherein concentration during respiration of the trace gas 1,1,1,2-tetrafluoroethane is about 1 vol. % to 5 vol. %, maximum of the inspired breathing gas volume present in the lungs.

15. A method according to claim 14, wherein concentration during respiration of the trace gas 1,1,1,2-tetrafluoroethane is 0.1 vol. % to 1 vol. % of the inspired breathing gas volume present in the lungs.

* * * * *